US010131641B2

(12) United States Patent
Sanders et al.

(10) Patent No.: US 10,131,641 B2
(45) Date of Patent: Nov. 20, 2018

(54) METHOD FOR PRODUCING TDI-TRIMERISATES WITH HIGH PURITY

(71) Applicant: Bayer MaterialScience AG, Monheim am Rhein (DE)

(72) Inventors: Josef Sanders, Leverkusen (DE); Andreas Hecking, Langenfeld (DE); Reinhard Halpaap, Odenthal (DE); Frank Richter, Leverkusen (DE); Oswald Wilmes, Cologne (DE); Jan Busch, Dusseldorf (DE); Tim Loddenkemper, Dormagen (DE); Friedhelm Steffens, Leverkusen (DE); Stefan Groth, Leverkusen (DE)

(73) Assignee: COVESTRO DEUTSCHLAND AG, Leverkusen (DE)

( * ) Notice: Subject to any disclaimer, the term of this patent is extended or adjusted under 35 U.S.C. 154(b) by 0 days.

(21) Appl. No.: 14/774,305

(22) PCT Filed: Mar. 7, 2014

(86) PCT No.: PCT/EP2014/054434
§ 371 (c)(1),
(2) Date: Sep. 10, 2015

(87) PCT Pub. No.: WO2014/139879
PCT Pub. Date: Sep. 18, 2014

(65) Prior Publication Data
US 2016/0031834 A1    Feb. 4, 2016

(30) Foreign Application Priority Data

Mar. 12, 2013    (EP) ..................... 13158688

(51) Int. Cl.
| *C08G 18/22* | (2006.01) |
| *C07D 251/30* | (2006.01) |
| *C08G 18/79* | (2006.01) |
| *C08G 18/02* | (2006.01) |
| *C09D 175/06* | (2006.01) |
| *C08G 18/42* | (2006.01) |
| *C09J 175/06* | (2006.01) |

(52) U.S. Cl.
CPC ......... *C07D 251/30* (2013.01); *C08G 18/022* (2013.01); *C08G 18/42* (2013.01); *C08G 18/794* (2013.01); *C09D 175/06* (2013.01); *C09J 175/06* (2013.01)

(58) Field of Classification Search
CPC .... C08G 18/022; C08G 18/42; C08G 18/794; C09D 175/06; C09J 175/06; C07D 251/30
See application file for complete search history.

(56) References Cited

U.S. PATENT DOCUMENTS

| 2,993,870 A | 7/1961 | Burkus |
| 3,394,111 A | 7/1968 | Liebsch |
| 3,996,223 A | 12/1976 | Gupta et al. |
| 4,115,373 A | 9/1978 | Henes et al. |
| 5,606,004 A | 2/1997 | Brahm et al. |
| 5,872,278 A | 2/1999 | Kraus et al. |
| 6,900,348 B1 | 5/2005 | Reif et al. |
| 6,936,678 B2 | 8/2005 | Brahm et al. |
| 6,992,186 B2 | 1/2006 | Brahm et al. |
| 2008/0287613 A1 | 11/2008 | Simon et al. |
| 2010/0249450 A1* | 9/2010 | Maeba ..................... B01D 3/14 560/352 |

FOREIGN PATENT DOCUMENTS

| CA | 2209139 A1 | 12/1997 |
| DE | 1 201 992 B | 9/1965 |
| DE | 24 52 532 A1 | 5/1976 |
| DE | 25 51 634 A1 | 6/1977 |
| DE | 4428107 A1 | 2/1996 |
| EP | 0 816 333 A1 | 1/1998 |
| EP | 0 866 057 A2 | 9/1998 |
| EP | 1 187 808 A1 | 3/2002 |
| EP | 1378529 A1 | 1/2004 |
| EP | 1378530 A1 | 1/2004 |
| EP | 1413571 A1 | 4/2004 |
| EP | 1 864 969 A1 | 12/2007 |
| WO | WO-0100569 A1 | 1/2001 |
| WO | WO-2005070984 A1 | 8/2005 |

OTHER PUBLICATIONS

International Search Report for PCT/EP2014/054434 dated May 20, 2014.
Paint and Coating Testing Manual, Fourteenth Edition of the Gardner-Sward Handbook, Josef V. Koleske, ASTM Manual Series MNL 17, ASTM Publication Code No. (PCN) 28-017095-14, pp. 115-116.
Gordon, Measure True Color, What is the Relationship between the APHA/Pt-Co/Hazen and Gardner, Oct. 22, 2012, pp. 1-2.
ASTM International, Designation: D 4663-98, Standard Test Method for Polyurethane Raw Materials: Determination of Hydrolyzable Chlorine of Isocyanates 1, pp. 1-2.
ASTM International, Designation D 4661-03, Standard Test Methods for Polyurethane Raw Materials: Determination of Total Chlorine in Isocyanates 1, pp. 1-2.

* cited by examiner

*Primary Examiner* — Michael L Leonard
(74) *Attorney, Agent, or Firm* — John E. Mrozinski, Jr.

(57) ABSTRACT

The invention relates to a novel method for producing polyisocyanurates comprising isocyanate groups, based on 2,4- and 2,6-toluylene diisocyanate (TDI) and to the use thereof in coating compositions.

9 Claims, No Drawings

METHOD FOR PRODUCING TDI-TRIMERISATES WITH HIGH PURITY

CROSS-REFERENCE TO RELATED APPLICATIONS

This application is a national stage application (under 35 U.S.C. § 371) of PCT/EP2014/054434, filed Mar. 7, 2014, which claims benefit of European Application No. 13158688.5, filed Mar. 12, 2013, both of which are incorporated herein by reference in their entirety.

The invention relates to a novel method for producing polyisocyanurates comprising isocyanate groups, based on 2,4- and 2,6-toluylene diisocyanate (TDI) and to the use thereof in coating compositions.

The production of polyisocyanurates comprising isocyanate groups has been known for a long time and described in a large number of publications and patents (Houben-Weyl, Methoden der organischen Chemie Volume 8, p. 136ff, Georg Thieme Verlag Stuttgart 1952; H. Wagner, H. F. Sarx, Lackkunstharze 5th Edition, page 153ff, Carl Hanser Verlag Munich 1971; DE-A 4 428 107, U.S. Pat. No. 2,993,870; DE-C 1 201 992; DE-A 2 452 532; J. prakt. Chem. 336, p. 185 to 200, 1994). Both trimerisates based on aliphatic and aromatic diisocyanates are used universally as coating raw materials and as polyurethane elastomers and polyurethane foams.

Commercial products are nowadays produced by trimerising industrially available mixtures of 2,4-TDI and 2,6-TDI in suitable organic solvents, with catalysis by means of phenolic catalysts comprising dialkylamino groups (Mannich bases), to almost complete conversion and then deactivating the catalyst by addition of acid-reacting substances or by reaction with alkylating agents. This deactivation is necessary because the products are otherwise not stable, which manifests itself by a fall in the NCO content and an increase in the viscosity over time.

For reasons of industrial hygiene, low-monomer trimerisate types are today preferred as products. These products are produced either by separating off excess monomer by distillation after the trimerisation reaction has taken place, or by controlling the trimerisation reaction to correspondingly high conversions, until the monomer has reacted as far as possible to higher oligomeric isocyanurates. The latter method is successful in particular when the diisocyanates used carry two significantly different reactive isocyanate groups —as in the case of 2,4-toluylene diisocyanate. Corresponding products comprising solvent can thus be produced with a content of monomeric TDI (sum of the isomeric toluylene diisocyanates) of <0.5% (e.g. Desmodur® IL, commercial product of Bayer AG, 50% strength in butyl acetate, NCO content: 8.0%).

However, the polyisocyanates of the prior art produced in this manner have the fundamental disadvantage that, as a result of their production, they are always contaminated by the stopped catalysts, the content thereof being greatly dependent on the reactivity of the toluylene diisocyanate used or on the amount of catalyst required in a particular case. This contamination by the stopped catalysts leads to more rapid yellowing and ageing of the polyisocyanates and of the coatings produced therewith.

The reason for the increased catalyst consumption and the resulting discoloration of the polyisocyanates and of the coatings produced therewith is in particular the use of TDI of insufficient purity. There has therefore been no lack of attempts to provide TDI grades with which lighter-coloured aromatic polyisocyanates which are more stable to ageing can be produced. For example, EP 1 413 571 describes a process with which a product fraction having a TDI content of at least 99.5% and less than 200 wt.ppm solvent and/or chlorinated aromatic hydrocarbons, less than 100 wt.ppm hydrolysable chlorine and less than 40 wt.ppm acid is obtained by preconcentrating the crude TDI solution to a solvent content of <20%, followed by fractionation in a dividing wall distillation column. In U.S. Pat. No. 6,900,348, or in the corresponding EP 1 187 808, it is described that lighter-coloured diphenylmethane diisocyanates can be obtained by using phosgene having a bromine content of <50 ppm. EP 0 816 333 claims a method for reducing the colour of TDI by treating the crude solution with hydrogen before the solvent is separated off.

Special pretreatment of the toluylenediamine (TDA) used to produce TDI can also lead to improved purity of the TDI. For example, EP 1 864 969 claims a method for producing lighter-coloured TDI in which the TDA used therefor in the phosgenation comprises less than 0.1 wt. % alkylated cyclic ketones, based on 100 wt. % TDA. In U.S. Pat. No. 5,872,278 or the corresponding EP 0 866 057, a method is described in which the amine used is treated with solids containing Lewis and/or Brönstedt acid centres before the reaction with phosgene. The isocyanates obtained then have a lighter colour than isocyanates produced using untreated amine.

Although these comparatively very complex methods permit the production of TDI grades with greater purity and a lighter colour, there is no indication therein of which secondary components are responsible for the increased catalyst consumption and the still insufficiently preventable discoloration of the polyisocyanates and of the coatings produced therewith, and how this discoloration can be prevented to a sufficient degree. There is therefore still an urgent need for light-coloured aromatic coating polyisocyanates which are stable to ageing.

The object of the present invention was, therefore, to find a method with which the content of stopped catalysts in the polyisocyanates can be reduced sufficiently that lighter-coloured polyisocyanates and coatings which are more resistant to ageing can be produced therewith.

It has been possible to achieve that object with the method described in greater detail below.

The invention is based on the surprising observation that catalyst consumption in the production of polyisocyanurates comprising isocyanate groups, based on toluylene diisocyanate can be reduced significantly if toluylene diisocyanate having a content of 2-chloro-6-isocyanato-methylcyclo-hexadienes (CIMCH) of <5 wt.ppm is used for their production. By means of the light-coloured polyisocyanurates produced by this method it is possible to produce lighter-coloured coatings which are more resistant to ageing. Light-coloured in this context means that the polyisocyanates so produced have API-1A colour indices of <100 Hazen, preferably <75-Hazen, particularly preferably <55 Hazen, measured on the basis of DIN EN 1557.

CIMCH can be in the form of 3 double bond isomers which can be present in the TDI in different ratios. These are formed, for example, in TDI production from 1-amino-2-methyl-cyclohexenone contained in the TDA used, which in turn can form in the production of TDA from dinitrotoluene (DNT) by partial nuclear hydrogenation of TDA and replacement of an amino functional group by water. It is also possible that the keto functional group is already introduced proportionately by oxidative attack in the production of DNT by nitration of toluene, there first being formed nitrocresols which can then form the above-described 1-aminomethyl-2-cyclohexenone in the subsequent hydrogenation.

Accordingly, the invention provides a method for producing polyisocyanates comprising solvent and/or diluent and isocyanurate groups, based on 2,4- and/or 2,6-toluylene diisocyanate, having a content of monomeric diisocyanate of <0.5 wt. %, based on polyisocyanate plus solvent, by trimerising A) from 20 to 80 wt. % of industrially available mixtures comprising substantially 2,4-toluylene diisocyanate and 2,6-toluylene diisocyanate comprising from 65 to 95 wt. % 2,4-toluylene diisocyanate and from 5 to 35 wt. % 2,6-toluylene diisocyanate in the presence of B) from 20 to 80 wt. % of solvents and/or diluents and C) phenolic catalysts comprising dialkylaminomethyl groups at a temperature of from 40 to 120° C. to almost complete conversion, and then deactivating the catalyst by addition of acid-reacting substances or by reaction with alkylating agents, characterised in that
the toluylene diisocyanate used has a content of 2-chloro-6-isocyanato-methylcyclohexadienes (CIMCH) of <5 wt.ppm.

Almost complete conversion means that the TDI used is reacted to a residual monomer content of <0.5 wt. %, based on polyisocyanate plus solvent.

The invention also provides polyisocyanates comprising solvent and/or diluent and isocyanurate groups produced by this method, as well as the use thereof as the polyisocyanate component in polyurethane coatings, in particular in two-component polyurethane coatings.

There come into consideration as the toluylene diisocyanate A) in particular 2,4-toluylene diisocyanate and commercial mixtures thereof with up to 35 wt. %, based on the mixture, of 2,6-toluylene diisocyanate, which have a content of 2-chloro-6-isocyanato-methylcyclohexadienes (CIMCH) of <5 wt.ppm. Such TDI grades can be obtained, for example, by purposive removal of 2-chloro-6-isocyanato-methylcyclohexadienes from the preconcentrated crude TDI solutions by distillation in a dividing wall distillation column, as is described in EP 1 413 571 B1. Particular preference is given, however, to toluylene diisocyanates which are produced by gas phase phosgenation of TDA and whose content of 2-chloro-6-isocyanato-methylcyclohexadienes is below the detection limit. Toluylene diisocyanate of such a grade is obtainable, for example, from Bayer Material Science AG from the production at the Caojing site in China.

Two independent analytical methods have been used for the clear characterisation of the component 2-chloro-6-isocyanato-methylcyclohexadienes. By means of gas chromatography techniques, different toluylene diisocyanate grades having a 2,4 content of about 80 wt. % were tested for their dissimilarities in the secondary component spectrum. By subsequent coupled gas chromatography-mass spectroscopy, a molecular weight of 169 g/mol was allocated to the three hitherto unknown compounds (CIMCH including two isomers). It was possible to obtain further structural information from the fragmentation in a manner known to the person skilled in the art. By means of complex nuclear resonance spectroscopy experiments ($^1$H-NMR, $^1$H-COSY, $^1$H-, $^1$H-TOCSY and $^1$H-, $^{13}$C-HMBC), the structures indicated below could be allocated to the three components with m/z 169.

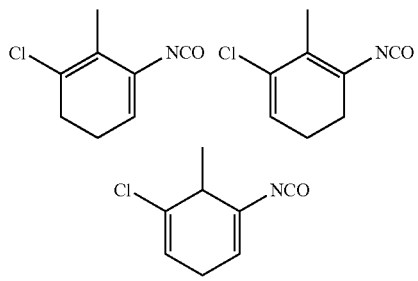

By purposive method development it was possible to set the detection limit of the isomers of CIMCH by means of gas chromatography-spectroscopy, using an Optima 5 HT column (60 m length, 0.25 mm inside diameter, 0.25 μm film thickness) from Macherey-Nagel in an HP Series 6890 gas chromatograph from Hewlett Packard, at 1 wt.ppm.

As solvents B) there can be used diluents and solvents conventional in polyurethane chemistry, such as, for example, toluene, xylene, cyclohexane, chlorobenzene, butyl acetate, ethyl acetate, ethyl glycol acetate, pentyl acetate, hexyl acetate, methoxypropyl acetate, tetrahydrofuran, dioxane, acetone, N-methylpyrrolidone, methyl ethyl ketone, white spirit, higher substituted aromatic compounds as are available commercially, for example, under the name Solvent Naphtha®, Solvesso®, Shellsol®, Isopar®, Nappar® and Diasol®, heavy benzol, tetralin, decalin and alkanes having more than 6 carbon atoms, conventional plasticisers, such as phthalates, benzoates, sulfonic acid esters and phosphoric acid esters, and mixtures of such diluents and solvents. The concentration of the diluent and solvent is adjusted to from 20 to 80 wt. %, preferably from 40 to 60 wt. %.

Also suitable as solvents B) are polyisocyanates based on aliphatic diisocyanates as are described, for example, in DE-A 4 428 107. Dilute low-monomer TDI trimerisates which do not comprise readily volatile solvents and diluents are obtainable therewith.

As phenolic catalysts C) for initiating and accelerating the trimerisation reaction there come into consideration as Mannich bases specific systems having a so-called negative temperature effect, which lead to a selective incorporation of TDI even at higher temperatures. Such catalyst systems have N,N-dialkylaminomethyl groups and phenolic OH groups bonded to aromatic systems. The alkyl groups are different or identical radicals each having up to 18 carbon atoms, which are optionally separated by oxygen or sulfur, or bridging alkyl groups in the form of an alkylene group having up to 18 carbon atoms optionally containing oxygen or sulfur. The N,N-dialkylaminomethyl groups and the phenolic OH groups can be distributed on a plurality of molecules or positioned on one or more benzene aromatic systems. Preferably, compounds that comprise both hydroxyl groups and dialkylaminomethyl groups in one molecule are used as catalyst systems.

Particular preference is given to the use of systems whose dialkylaminomethyl groups are in the ortho-position relative to aromatic hydroxyl groups, the alkyl groups being identical or different C1- to C3-alkyl radicals.

The synthesis of suitable Mannich bases is described, for example, in DE 25 51 634 A1 and WO 2005 70984 A1. Mannich bases which are preferably to be used are those based on phenol, p-isononylphenol or bisphenol A, which are obtained by reaction with dimethylamine and formaldehyde, for example according to DE-A 2 452 531 or Synth.

Commun. (1986), 16, 1401-9. Mannich bases based on phenol or bisphenol A are particularly preferred.

The catalysts C) are used in the form of the pure substance or in solution optionally in a plurality of small portions or continuously, in total, from 0.1 to 0.8 wt. %, preferably from 0.3 to 0.6 wt. %, catalyst is used for the production.

The trimerisation reaction according to the invention is carried out according to known methods, as are described, for example, in WO 2005 70984 A1.

The trimerisation is carried out in the presence of the solvent and/or diluent component B). The trimerisation reaction takes place in the temperature range of from 40 to 120° C., preferably from 50 to 70° C., The reaction time is generally from 5 to 48 hours, preferably from 10 to 24 hours. If the content of free TDI in the reaction mixture is below 0.5 wt. %, the trimerisation is terminated by thermal decomposition of the catalyst or, preferably, by addition of a catalyst poison. Suitable catalyst poisons are protonic acids such as dibutyl phosphate or acylating and alkylating agents such as isophthalyl acid dichloride or toluenesulfonic acid methyl ester.

Surprisingly, less catalyst is consumed in the method according to the invention, with from 0.1 to 0.8 wt. % catalyst, than when conventional TDI is used, so that lighter-coloured polyisocyanates which are more stable to yellowing are obtained.

Furthermore, when the trimerisation reaction is complete, a further modification of the product with low molecular weight or/and polymeric compounds comprising hydroxyl groups can take place.

The polyisocyanates produced by the method according to the invention are preferably used in the production of coating materials which can be cured under the effect of atmospheric moisture, They can likewise be used in the production of adhesion promoters, adhesives, printing inks, scaling materials and polyurethane moulded articles. They are particularly preferably used as crosslinkers in 2-component systems with isocyanate-reactive compounds known per se. These include, for example, hydroxy-functional polyethers, polyesters, polyamides, polycarbonates, polyacrylates, polybutadienes or mixed types of the mentioned hydroxy-functional polymers. Low molecular weight diols and polyols, dimer and trimer fatty alcohols as well as amino-functional compounds can also be used in 2K systems. Using blocked isocyanate-reactive compounds, one-component systems can also be formulated; likewise, the products produced by the method according to the invention can also be used in blocked form as or in coating materials, Drying thereby takes place at higher temperatures up to about 200° C.

In addition to the products according to the invention, there can also be used in the coatings other auxiliary substances and additives such as, for example, conventional wetting agents, flow agents, anti-skinning agents, antifoams, solvents, mattifying agents such as, for example, silica, aluminium silicates and high-boiling waxes, viscosity-regulating substances, pigments, colourants, UV absorbers, stabilisers against thermal or oxidative degradation.

The coating materials obtained can be used in the coating of any desired substrates such as, for example, wood, plastics, leather, paper, textiles, glass, ceramics, plaster, masonry, metals or concrete. They can be applied by conventional methods of application such as spraying, spread coating, flood coating, pouring, dipping, roller coating. The coating compositions can be used in the form of clear coatings and also in the fat fit of pigmented coatings.

The coatings produced from the products according to the invention cure at 20° C. generally within a period of from several minutes to hours to form high-quality coatings. Curing can, however, also take place at lower temperatures (down to −5° C.) or in an accelerated manner at higher temperatures up to 200° C.

EXAMPLES

In the examples which follow, all percentages are by weight. The following methods were used to characterise the products obtained:

The NCO content of the resins described in the examples and comparative examples was determined by titration according to DIN EN ISO 11 909.

The dynamic viscosities were measured according to DIN 3219 with a DIN measurement body 125 at 23° C. using a Reolab QC viscometer from Anton Paar in the shear rate range of from 1 to 1600 l/s.

The residual monomer contents were determined by gas chromatography according to DIN EN ISO 10283.

The solids content (non-vaporizable portion) was determined according to DIN 3251 under the test conditions described therein for isocyanates.

The colour indices were measured at 23° C. on the basis of DIN EN 1557 using a LICO 400 from HACH Lange in 50 mm disposable rectangular cuvettes.

Example 1

In Accordance with the Invention 426.0 g of a commercial mixture of 2,4- and 2,6-toluylene diisocyanate in the ratio 4:1 and having a content of CIMCH of 4.8 wt.ppm are placed together with 436.5 g of butyl acetate in a 1000 ml double-jacketed ground glass vessel flushed with nitrogen. The reaction mixture is heated to the desired reaction temperature of 75° C. The trimerisation reaction is started by the continuous addition of 7.5 g/h of a 30 wt. % activator solution (xylene) of a Mannich base based on bisphenol A/formalin/dimethylamine. When the trimerisation reaction has noticeably started, the continuous metered addition of activator is interrupted in order safely to dissipate the reaction energy that is liberated. When the desired reaction temperature is reached again, the metered addition of activator is continued. After about 7.5 hours, the entire amount of activator solution of 21 g has been metered in, and stirring is then carried out for about 12 hours, while maintaining the previous reaction temperature, until the desired NCO content is reached. In order definitely to end the trimerisation reaction, the molar 1.15-fold amount of toluenesulfonic acid methyl ester (TSE) is added to the reaction mixture. After addition of 12.2 g of TSE, the reaction product is stirred for one hour at 80° C. The polyisocyanate comprising solvent and isocyanurate groups so obtained has the following characteristic values:

NCO content=7.97 wt. %
Viscosity 1290 mPa*s@23° C.
Residual monomer content=0.14 wt. %
Solids content=51.2 wt. %
APHA colour index=73 Hazen Example 2

In Accordance with the Invention

The procedure is analogous to Example 1, but the reaction is carried out with toluylene diisocyanate having a 2,4 content of about 80 wt. % which was produced by gas phase phosgenation, and a content of CIMCH below the detection limit (<1 wt.ppm). In order to achieve the desired NCO content, only 15.3 g of the identical 30 wt. % activator solution are required. An amount of TSE of 7.6 g is used for the deactivation. The polyisocyanate comprising solvent and isocyanurate groups so obtained has the following characteristic values:
NCO content=8.06 wt. %
Viscosity=1240 mPa*s@23° C.
Residual monomer content=0.07 wt. %
Solids content=51.1 wt. %
APHA colour index=53 Hazen Example 3

Not in Accordance with the Invention

Using a toluylene diisocyanate grade having a 2,4 content of about 80 wt. % which has a content of CIMCH of 160 wt.ppm, the procedure is analogous to Example 1, but 33.6 g of the 30 wt. % activator solution mentioned in Example 1 are required for the desired reaction conversion, whereby the deactivation is carried out by addition of 19.6 g of toluenesulfonic acid methyl ester. The polyisocyanate comprising solvent and isocyanurate groups so obtained has the following characteristic values:
NCO content=8.03 wt. %
Viscosity=1150 mPa*s@23° C.
Residual monomer content=0.17 wt. %
Solids content=51.3 wt. %
API-IA colour index=140 Hazen Example 4

Not in Accordance with the Invention

The procedure is analogous to Example 1, but the reaction is carried out with toluylene diisocyanate having a 2,4 content of about 80 wt. %, which has a content of CIMCH of 60 wt.ppm. In order to achieve the desired NCO content, an amount of 28.5 g of 30 wt. % activator solution is required. The reaction mixture is deactivated by addition of 16.6 g of toluenesulfonic acid methyl ester. The polyisocyanate comprising solvent and isocyanurate groups so obtained has the following characteristic values:
NCO content=8.03 wt. %
Viscosity=1300 mPa*s@23° C.
Residual monomer content=0.20 wt. %
Solids content=51.0 wt. %
APHA colour index=125 Hazen Application Example Yellowing of a Coating Formulation The polyisocyanates from Example 1 and Example 4 are each mixed in the NCO/OH ratio 0.7:1 with a commercially available polyester polyol (®Desmophen 1300, commercial product from Bayer AG, hydroxyl content 4 wt. %) to give a total concentration of 40 wt. % in butyl acetate. The formulations so obtained are applied wet to a standardised white plate with a layer thickness of 180 μm. The coatings so applied are dried for 7 days at room temperature, which is defined as yellowing time t=0. When the 0 value has been determined, the unprotected plates are subjected to natural weathering and measured again according to previously determined time intervals (see Table 1). All the measurements were carried out by means of a Color-Guide 45°/0° colorimeter (BYK-Gardner). The colour changes are summarized in Table 1, the total colour difference is expressed in the manner known to the person skilled in the art as $\Delta E^*$.

| Sample | $\Delta E^*$ 7 days | $\Delta E^*$ 14 days | $\Delta E^*$ 1 month | $\Delta E^*$ 3 months | $\Delta E^*$ 6 months |
|---|---|---|---|---|---|
| Polyisocyanate from Example 1 CIMCH $5 \times 10^{-4}$ wt. % | 1.51 | 2.42 | 5.36 | 9.42 | 13.66 |
| Polyisocyanate from Example 2 CIMCH $<10^{-5}$ wt. % | 1.51 | 2.41 | 5.30 | 8.71 | 12.42 |
| Polyisocyanate from Example 3 CIMCH $1.6 \times 10^{-2}$ wt. % | 1.62 | 2.85 | 6.92 | 15.11 | 15.02 |
| Polyisocyanate from Example 4 CIMCH $6 \times 10^{-3}$ wt. % | 1.58 | 2.76 | 6.58 | 12.86 | 24.78 |

The application examples show that the coating formulations produced using the polyisocyanates according to the invention from Examples 1 and 2 have significantly greater colour stability.

The invention claimed is:
1. A method for producing polyisocyanates comprising solvent or diluent and isocyanurate groups, based on 2,4- and/or 2,6-toluylene diisocyanate, having a content of monomeric diisocyanate of <0.5 wt. %, based on polyisocyanate plus solvent, comprising trimerising
   A) from 20 to 80 wt. % of a mixture comprising 2,4-toluylene diisocyanate and 2,6-toluylene diisocyanate comprising from 65 to 95 wt. % 2,4-toluylene diisocyanate and from 5 to 35 wt. % 2,6-toluylene diisocyanate in the presence of
   B) from 20 to 80 wt. % of solvents or diluents and
   C) a phenolic catalyst comprising dialkylaminomethyl groups at a temperature of from 40 to 120° C. to almost complete conversion, and then deactivating the catalyst by addition of an acid-reacting substance or by reaction with an alkylating agent, wherein the toluylene diisocyanate has a content of 2-chloro-6-isocyanato-methylcyclohexadienes (CIMCH) of <5 wt.ppm and wherein the polyisocyanates comprising solvent or diluent and isocyanurate groups have APHA colour indices <100 Hazen.
2. The method according to claim 1, wherein the toluylene diisocyanate is produced by gas phase phosgenation.
3. The method according to claim 1, wherein the toluylene diisocyanate has a content of 2-chloro-6-isocyanato-methylcyclohexadienes below the detection limit of 1 wt.ppm.
4. The method according to claim 1, wherein the catalysts is obtained as Mannich base based on phenol or bisphenol A by reaction with dimethylamine and formaldehyde.
5. The method according to claim 1, wherein the catalyst is deactivated by dibutyl phosphate or p-toluenesulfonic acid methyl ester.
6. The polyisocyanates produced by the method according to claim 1 comprising solvent or diluent and isocyanurate groups.
7. A method comprising utilizing the polyisocyanate produced according to the method of claim 6 as the polyisocyanate component in polyurethane coatings.
8. The method according to claim 7 wherein the polyisocyanates comprise a crosslinker in two-component polyurethane coatings.

9. A polyurethane adhesive comprising the polyisocyanates produced according to the method of claim 6.

* * * * *